(12) United States Patent
Chen et al.

(10) Patent No.: US 7,672,427 B2
(45) Date of Patent: *Mar. 2, 2010

(54) IMAGING SYSTEM

(75) Inventors: Zhiqiang Chen, Beijing (CN); Li Zhang, Beijing (CN); Hewei Gao, Beijing (CN); Kejun Kang, Beijing (CN); Jianping Cheng, Beijing (CN); Yuanjing Li, Beijing (CN); Yinong Liu, Beijing (CN); Yuxiang Xing, Beijing (CN); Ziran Zhao, Beijing (CN); Yongshun Xiao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 96 days.

This patent is subject to a terminal disclaimer.

(21) Appl. No.: 11/545,255

(22) Filed: Oct. 10, 2006

(65) Prior Publication Data
US 2007/0116177 A1 May 24, 2007

(30) Foreign Application Priority Data
Nov. 21, 2005 (CN) ........................ 200510123587.6

(51) Int. Cl.
*G01N 23/04* (2006.01)
(52) U.S. Cl. ........................................ 378/57
(58) Field of Classification Search ............... 378/4–20, 378/21, 57, 901
See application file for complete search history.

(56) References Cited
U.S. PATENT DOCUMENTS
4,599,740 A * 7/1986 Cable .......................... 378/57

(Continued)

FOREIGN PATENT DOCUMENTS
JP 6-27249 2/1994

(Continued)

OTHER PUBLICATIONS

Gao et al., Direct Filtered-backprojection-type Reconstruction from a Straight-line Trajectory, Optical Engineering, vol. 46(5), May 2007, pp. 057003-1 to 057003-11.*

(Continued)

*Primary Examiner*—Edward J Glick
*Assistant Examiner*—Alexander H Taningco
(74) *Attorney, Agent, or Firm*—Westman, Champlin & Kelly, P.A.

(57) ABSTRACT

It is disclosed an imaging system comprising: radiation generating means including at least one radiation source for generating radiations; data acquiring means including an detector matrix faced the radiation source for obtaining projection data by receiving radiations penetrated through an object to be inspected; transporting means for making the object to be inspected between the radiation source and the detector matrix linearly moving relative to the radiation source and the detector matrix; and controlling and image processing means for controlling the radiation generating means, the data acquiring means and the transporting means, and for reconstructing an image of the object to be inspected from the projection data. The imaging system according to the present invention achieves a real stereoscopic radiography by using straight-line trajectory scan and reconstructing a tomographic or stereoscopic image through a straight-line filtered back-projection algorithm. The present imaging system has advantages of fast examination speed, no rotation, and out of large cone-angle problem in a circular-orbit cone-beam CT.

12 Claims, 7 Drawing Sheets

U.S. PATENT DOCUMENTS

| | | | | |
|---|---|---|---|---|
| 4,789,929 | A | * | 12/1988 | Nishimura et al. ............ 378/15 |
| 5,602,890 | A | * | 2/1997 | Gray et al. .................... 378/57 |
| 5,745,542 | A | * | 4/1998 | Gordon et al. ................. 378/4 |
| 5,802,134 | A | * | 9/1998 | Larson et al. .................. 378/4 |
| 6,324,249 | B1 | * | 11/2001 | Fazzio ......................... 378/22 |
| 6,751,284 | B1 | * | 6/2004 | Claus et al. ................... 378/22 |
| 6,928,137 | B2 | * | 8/2005 | Bruder et al. .................. 378/4 |
| 6,954,515 | B2 | * | 10/2005 | Bjorkholm et al. .......... 378/137 |
| 7,162,005 | B2 | * | 1/2007 | Bjorkholm .................... 378/57 |
| 2002/0037068 | A1 | * | 3/2002 | Oikawa ......................... 378/15 |
| 2004/0017888 | A1 | * | 1/2004 | Seppi et al. .................... 378/57 |
| 2004/0179643 | A1 | * | 9/2004 | Gregerson et al. ............. 378/4 |
| 2004/0213375 | A1 | * | 10/2004 | Bjorkholm et al. ............ 378/58 |
| 2004/0258194 | A1 | * | 12/2004 | Chen et al. ..................... 378/4 |
| 2005/0169422 | A1 | * | 8/2005 | Ellenbogen ................... 378/57 |
| 2006/0067458 | A1 | * | 3/2006 | Chen ............................. 378/4 |

FOREIGN PATENT DOCUMENTS

JP         2005-257398         9/2005

JP         2005-265618         9/2005

OTHER PUBLICATIONS

Gao et al., Volumetric Imaging from a Multisegment Straight-line Trajectory and a Practical Recontruction Algorithm, Optical Engineering, vol. 46(7), Jul. 2007, pp. 077004-1 to 077004-10.*

Yu et al., Asymmetric Fan-beam Configurations with Spatially Varying Focal Lengths and Shift-Variant Filtering Reconstruction, Optical Engineering, vol. 43(10), Oct. 2004, pp. 2340-2347.*

Smith et al., Fan-beam Reconstruction from a Straight Line of Source Points, IEEE Transactions on Medical Imaging, vol. 12, No. 1, Mar. 1993, pp. 10-18.*

Bleuet et al., An Adapted Fan Volume Sampling Scheme for 3-D Algebraic Reconstruction in Linear Tomosynthesis, IEEE Transactions on Nuclear Science, vol. 49, No. 5, Oct. 2002, pp. 2366-2372.*

Sidky et al., Volume Image Reconstruction from a Straight-line Source Trajectory, IEEE Nuclear Science Symposium Conference Record, Mar. 2005, pp. 2441-2308.*

"An Adapted Fan Volume Sampling Scheme for 3D Algebraic Reconstruction in Linear Tomosynthesis", by P. Bleuet et al., *IEEE*, 2002, pp. 1720-1724.

"Fan-Beam Reconstruction From a Straight Line of Source Points", by B. Smith et al., *IEEE*, 1993, pp. 10-18.

"Scanning of Logs with Linear Cone-Beam Tomography", by M. Magnusson et al, *Computers and Electronics in Agriculture*, 2003, pp. 45-62.

\* cited by examiner (A) (B)

(C) (D)

(A)
 (B)
 (C)
 (D)

(A)

(B)

IMAGING SYSTEM

The present application claims priority of Chinese patent application Serial No. 200510123587.6, filed Nov. 21, 2005, the content of which is hereby incorporated by reference in its entirety.

BACKGROUND OF THE INVENTION

1. Field of the Invention

The present invention relates to the radiographic technology, and more particularly to an imaging system using a straight-line trajectory scan to improve the speed of a radiographic security inspection.

2. Description of the Prior Art

Security inspection is much more significant in anti-terrorism and anti-drug-smuggles. After 911, US makes more and more account of the security inspection in public places such as airports and railway stations. In addition, with the development of anti-drug-smuggles, the requirements for inspecting containers and luggage at Custom are increased.

Current security inspection systems are mainly radiographic systems, and in the radiography field, radioscopic system such as DR (digital radiography) is commonly used, while stereo-imaging equipment such as CT (computed tomography) system is not widely employed. This is because a practical security inspection system generally performs an on-line real-time inspection and thus a fast scanning and imaging speed of the inspection system is required. For example, for civil aviation luggage inspection, a custom clearance rate of 0.5 m/s is required. However, this requirement can hardly be satisfied currently even if a spiral CT with a large pitch is employed. Further more, in regard to some large objects such as custom containers, it is very difficult to rotate the containers or the radiation source and the detectors. Besides, the cost of devices for the CT system is quite high. These above and other factors prevent the CT system from being widely used in the security inspection field. However, compared with the CT systems, a radioscopic system has a drawback of no ability of avoiding an overlapping effect of objects in a radiation direction, and thus the inspection capability is restrained so that a real stereoscopic inspection and location can not be performed well.

With the development of CT techniques, a tomographic image having a certain quality can be reconstructed in a case of situation where a limited angle projection data is obtained or the data is truncated. Thus, it becomes practical to apply an incompletely scan and reconstruct an approximate images. Theoretically, for an imaging system with a straight-line trajectory, if the length of scanning trajectory is infinite, an exact reconstruction could be achieved. If the trajectory is of a finite length, then it is equivalent to a limited-angle CT scan. Therefore, by using CT reconstructions dealing with incomplete data, cross-section images can be obtained from a straight-line imaging system, and the stereoscopic radiography is achieved.

An imaging system with a straight-line trajectory, Computed Laminography system, has already been proposed. However, it has a small range of the source coverage and reconstruction algorithms for tomosynthesis are used, which results in a poor capability of three-dimension imaging. Consequently, an imaging system capable of speedily achieving the three-dimension imaging and tomographic images is required.

SUMMARY OF THE INVENTION

In view of the above problems, the present invention is done. It is an object of the present invention to provide an imaging system using a straight-line trajectory which can obtain both a DR image and a tomographic image, and solve the problem of object overlapped problem in the perspective imaging so as to speedy achieve a stereoscopic radiography in the security inspection.

In one aspect of the present invention, there is provided an imaging system comprising: radiation generating means including at least one radiation source for generating radiations; data acquiring means including a detector matrix opposite to the radiation source for obtaining projection data by receiving radiation photos penetrated through an scanning object; transporting means for making the object between the radiation source and the detector matrix linearly moving relative to the radiation source and the detector matrix; and controlling and image processing means for controlling the radiation generating means, the data acquiring means and the transporting means, and for reconstructing an image of the object to be inspected from the projection data.

According to an embodiment of the present invention, a horizontal range of projection angles covered by the radiation generating means and the detector matrix is more than 90 degree.

According to an embodiment of the present invention, the detector matrix comprises a plannar detector containing a plurality of detector elements.

According to an embodiment of the present invention, the detector matrix comprises a collinear detector provided vertically and containing a plurality of detector elements.

According to an embodiment of the present invention, the detector matrix further comprises another collinear detector provided horizontally and containing a plurality of detector elements.

According to an embodiment of the present invention, the collinear detector horizontally provided has a variable position in the vertical direction.

According to an embodiment of the present invention, the controlling and image processing means includes: a projection data conversion section for converting the projection data into projection data under quasi-parallel-beam scan; a filtration section for obtaining filtered projection data by convoluting the projection data under quasi-parallel-beam scan with a predetermined convolutional kernel; and a back-projection section for reconstructing the image by back-projecting the filtered projection data with a weighting factor.

According to an embodiment of the present invention, the plurality of detector elements are arranged in accordance with one and the same spacing interval.

According to an embodiment of the present invention, the projection data conversion section reverses and shifts the projection data $p(l,t,z)$ to obtain the projection data $q(l,t,z)$ under quasi-parallel-beam scan, wherein the projection data $p(l,t,z)$ denotes a projection value at a coordinate t in the $z^{th}$ slice of the detector when the object relatively moves to a coordinate l on the line; the filtration section performs one-dimension convolution of the projection data $q(l,t,z)$ under quasi-parallel-beam scan with the predetermined convolutional kernel in the l direction to obtain the filtered projection data $Q(l',t,z)$; and the back-projection section back-projects the filtered projection data $Q(l',t,z)$ with a weighting factor along the radiation projection direction to obtain the reconstructed image.

According to an embodiment of the present invention, the plurality of detector elements are arranged with regard to the radiation source in accordance with one and the same angular interval.

According to an embodiment of the present invention, the projection data conversion section reverses and shifts the projection data $p(l,\gamma,z)$ to obtain the projection data $q(l,\gamma,z)$ under quasi-parallel-beam scan, wherein the projection data $p(l,\gamma,z)$ denotes a projection value at an angular position of $\gamma$ in the $z^{th}$ slice of the detector when the object relatively moves to a coordinate l on the line; the filtration section performs one-dimension convolution of the projection data $q(l,\gamma,z)$ under quasi-parallel-beam scan with the predetermined convolutional kernel in the l direction to obtain the filtered projection data $Q(l',\gamma,z)$; and the back-projection section back-projects the filtered projection data $Q(l',\gamma,z)$ with a weighting factor along the radiation projection direction to obtain the reconstructed image.

According to an embodiment of the present invention, the plurality of detector elements are solid detector elements, gas detector elements or semiconductor detector elements.

According to an embodiment of the present invention, the radiation source is an X-ray accelerator, an X-ray tube or a radioisotope.

The imaging system according to the present invention achieves a real stereoscopic radiography by using a straight-line trajectory scan and reconstructing a tomographic or stereoscopic image through a straight-line filtered back-projection algorithm. The present imaging system has advantages of fast examination speed, no rotation, and out of problems such as large cone-angle problem in cone-beam CT systems. Therefore, the inventive imaging system may be potentially used in the fast security inspection field and large object inspection field.

DETAILED DESCRIPTION OF THE PREFERRED EMBODIMENTS

Hereafter, the embodiments of the present invention will be described in detail with reference to the accompanying drawings.

First Embodiment

Figure 1:
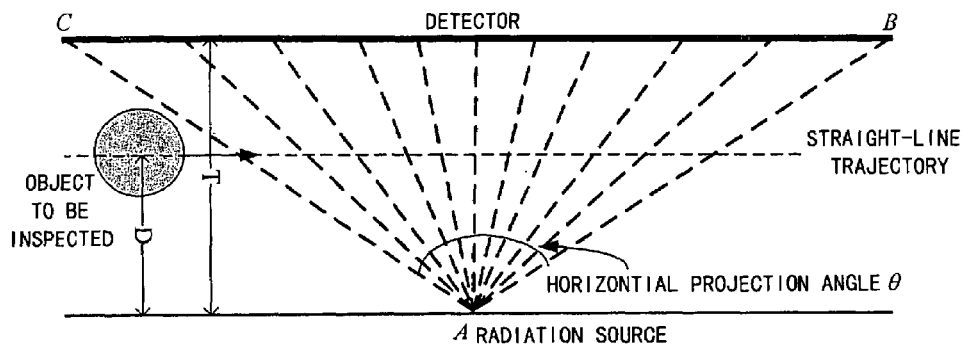
FIG. 1 is a plane diagram of straight-line trajectory scan performed in the imaging system according to the present invention.
Figure 2:
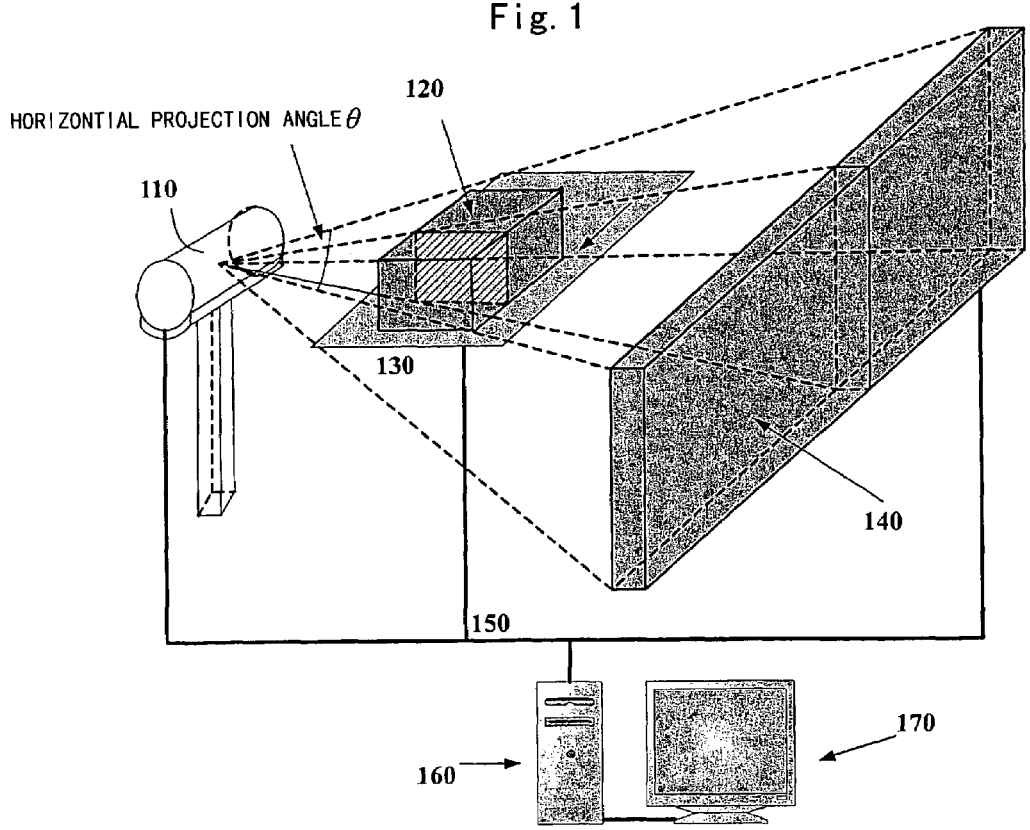
FIG. 2 is a structural diagram of the imaging system according to the first embodiment of the present invention.

FIG. 1 is a plane diagram of straight-line trajectory scan performed in the imaging system according to the present invention. FIG. 2 is a structural diagram of the imaging system according to the first embodiment of the present invention.

As shown in FIG. 1, an object to be inspected moves between a radiation source A and a detector along a straight line. During the process of movement, the radiation source A emits radiations according to commands from a control system, which penetrates the object to be inspected. The detector receives transmitted signals, acquires projection data under the control of the control system, and stores the projection data into a memory.

The imaging system as shown in FIG. 2 comprises a radiation generating unit 110, a transporting unit 130, a data acquiring unit 140, a control and data signal bus 150, a controlling and image processing unit 160, and a display 170.

As shown in FIG. 2, the radiation generating unit 110 for example includes an X-ray accelerator, an X-ray tube or a radioisotope, and respective assistant devices. In order to make a horizontal range of projection angles more than 90 degree, for example, between 90 and 180 degree, two or more radiation sources may be employed and chosen according to the size of the object 120 to be inspected and the application environment.

The transporting unit 130 such as a conveying belt may carry and transport the object 120 to be inspected stably, so as to make the carried object 120 to be inspected moving along a straight line during inspections. Or, the transporting unit 130, during inspections, makes the radiation source and the detector moving along a straight line, or makes the object to be inspected as well as the radiation source and the detector moving in opposite directions. That is to say, the movement of the object to be inspected and that of the radiation source and the detector are relative and equivalent to each other. Although in the following description, the object to be inspected moves while the radiation source and detector remain still, it is also possible that the radiation source and detector move while the object to be inspected remains still.

The data acquiring unit 140 which is mainly detector matrix is used to acquire transmitted projection data of the cone-beam scan by receiving radiations penetrated through the object to be inspected. The data acquiring unit 140 further includes a readout circuit for reading out the projection data from the detector matrix and a logic control unit etc. (not shown). The detector matrix may be composed of a plurality of solid detector elements, a plurality of gas detector elements or a plurality of semiconductor detector elements. It is not necessary to arrange respective detector elements closely but they should be on one and the same straight line in X-axis direction (that is, the movement direction of the object to be inspected).

In general, a total length of one row of detector arrays is (K), that is, segment BC shown in FIG. 1, which is associated with the distance (T) from the center of the detector array to the radiation source and the total range of projection angles. In a case where the range of projection angles (θ) is determined, the longer the distance T is, the longer the total length of the detector array is required, and the following relationship is satisfied:

$$K = 2T\tan\frac{\theta}{2}.$$

Further, the detector matrix needs to be positioned on an opposite side to the radiation source, has a range of projection angles more than 90 degree in the horizontal direction, and covers the object in the vertical direction. Thus, a CT reconstruction for limited angle situation can be achieved (with a good reconstructed image quality). This detector matrix can be a plannar detector or a collinear one.

During data acquiring, it is necessary that a sampling interval (Δt) is uniform on the time axis, and the object to be inspected moves uniformly. Assuming that the moving velocity is v, then an equivalent space sampling interval of the imaging system according to the present invention is:

Δd=vΔt.

Also, it is necessary that all the detector elements perform acquisition synchronously, and the data acquired per time make up of one slice of the projection data. After multiple collections (generally, several hundreds to thousands times), the volumetric projection data are formed. The stereoscopic image reconstructed in the controlling and image processing unit is based on these data, and so is the displaying of the perspective image.

When the perspective image is required, only those projection data acquired by the central column of the detector matrix are output, and the imaging principle thereof is the same as that of the existing radioscopic imaging.

The control and data signal bus 150 is used to transmit control and data signals.

The controlling and image processing unit 160 controls each of the radiation generating unit 110, the transporting unit 130 and the data acquiring unit 140 through the control and data signal bus 150.

During a scanning, the controlling and image processing unit 160 controls the transporting unit 130 to make the object 120 to be inspected moving along a straight line, orders the radiation generating unit 110 to generate radiations, controls the data acquiring unit 140 to receive the transmitted signals and generate the projection data, and performs post-processes to the generated projection data.

Therefore, the object 120 to be inspected moves uniformly along the straight-line trajectory shown in FIG. 1. The data acquiring unit 140 samples synchronously and with a constant time interval to obtain the projection data.

Figure 3:
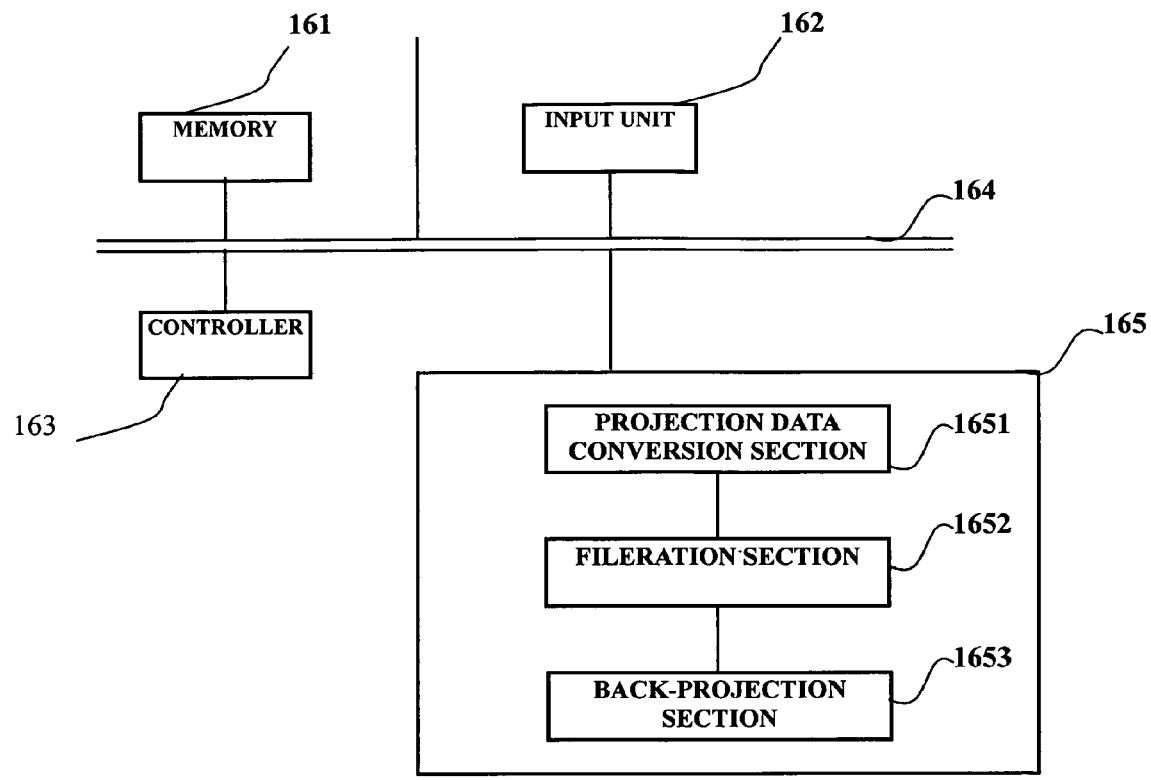
FIG. 3 is a functional block diagram of the controlling and image processing unit in the imaging system shown in FIG. 2.

FIG. 3 is a functional block diagram of the controlling and image processing unit 160 in the imaging system shown in FIG. 2. As shown in FIG. 3, the controlling and image processing unit 160 includes a memory 161 which is a storage medium such as hard disk and the like for storing data; an input unit 162 which is an input means such as keyboard for facilitating users to input parameters or commands; a controller 163 for, after the user inputs a command through the input unit 162, instructing the transporting unit 130 to make the object 120 to be inspected moving uniformly along a straight line, and the radiation generating unit 110 and data acquiring unit 140 to start working in order to obtain the projection data; an internal bus 164 for connecting each units and transmitting the control signals and data; and an image reconstruction unit 165 for performs reconstruction on the projection data obtained by the data acquiring unit 140.

Figure 4:
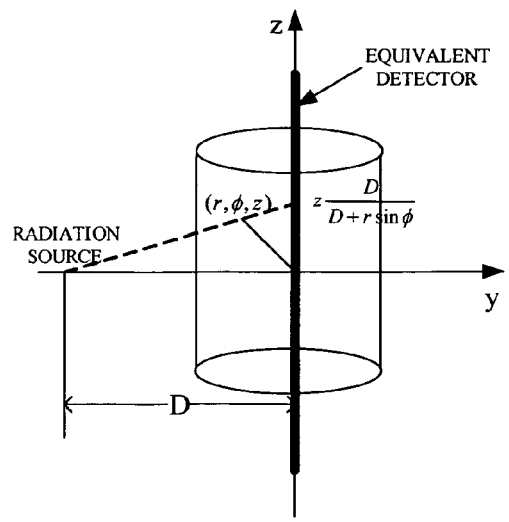
FIG. 4 is a schematic diagram showing the geometric relationship between the equivalent detector and the object point to be reconstructed in the Z direction.

The image reconstruction process will be described in detail referring to FIG. 4. FIG. 4 is a schematic diagram showing the geometric relationship between the equivalent detector (the real detector is imaged onto the central line of the linear movement of the object) and the point of interest of object to be reconstructed in Z direction.

Assuming that an approximate estimation for the object function $f(r,\phi,z)$ to be inspected is denoted as $\hat{f}(r,\phi,z)$, then the following equation is hold:

$$\hat{f}(r,\phi,z) = \int_{-t_m}^{t_m} \frac{1}{\sqrt{D'^2+t^2}} Q\left(l', t, z\frac{D}{D+r\sin\phi}\right) dt \quad (1)$$

wherein, $$Q(l', t, z) = \int q(l, t, z)h(l'-l)dl \quad (2\text{-}1)$$

$$q(l, t, z) = p(-l+t, t, z) \quad (2\text{-}2)$$

$$l' = -r\cos\phi + \frac{tr\sin\phi}{D} \quad (3)$$

$$D' = \sqrt{D^2 + \left(z\frac{D}{D+r\sin\phi}\right)^2} \quad (4)$$

Here, the detector elements in the detector matrix are arranged with a constant spacing interval, and the data p(l,t,z) denotes a projection value at a coordinate of t in the $z^{th}$ slice of the detector matrix when the object 120 to be inspected moves to a coordinate of l on the line. It should be noted that t and z are both equivalent values of each detector element of the detector matrix onto the central line of the linear movement of the object.

In addition, in Equations (1)-(4), D denotes a distance from the radiation source in the radiation generating unit 110 to the central line of the linear movement; The notation ±$t_m$ represents a minimum and a maximum positions of the detector matrix in the X-axis direction; h is a convolutional kernel, and its theoretical value is $$h(l) = \int_{-\infty}^{\infty} |\omega| e^{j2\pi\omega l} d\omega,$$

generally, an S-L type kernel is used, a discrete form of this kernel is:

$$h(n) = \frac{-2}{\pi^2(4n^2-1)}, n = 0, \pm 1, \pm 2, \ldots \quad (5)$$

Therefore, in the image reconstruction unit 165, a projection data conversion section 1651 reverses and shifts the projection data p(l,t,z) to obtain q(l,t,z), wherein q(l,t,z) denotes projection data under quasi-parallel-beam scan. The meaning of the term "quasi-parallel-beam scan" is that for respective angles, the equivalent sampling intervals of the detector elements are different, and the scanned angular samples may not uniform either.

Thereafter, a filtration section 1652 performs one-dimension convolution of the projection data q(l,t,z) under quasi-parallel-beam scan with the convolutional kernel h in the l direction to obtain filtered projection data Q(l',t,z).

Next, a back-projection section 1653 back-projects the filtered projection data Q(l',t,z) with a weighting factor along the radiation projection direction to obtain the reconstructed image.

Here, it should be noted that the object of reversing and shifting is to convert the projection data from a straight-linear trajectory scan into the projection data under quasi-parallel-beam scan. The quasi-parallel-beam scan is not the parallel-beam scan in a standard CT because for each of the respective angles, the equivalent sampling intervals of the detector elements are different, and the angular samples may not uniform either.

In addition, the object of filtration with the convolutional kernel h is the same as in a standard FBP (filtered back-projection) reconstruction algorithm, the reconstruction image can be achieved from the filtered projection data Q(l', t,z) after weighted back-projection.

Therefore, in the present invention, the filtration is performed in the data acquiring direction l, and the back-projection is performed in the radiation direction. As compared with the algorithm of rebinning-to-parallel-beam and standard parallel-beam FBP, the present invention can fully utilize each of the valid data, improves the image spatial resolution, and is less sensitive to data truncation than the rebinning-to-parallel-beam algorithm.

Figure 5:
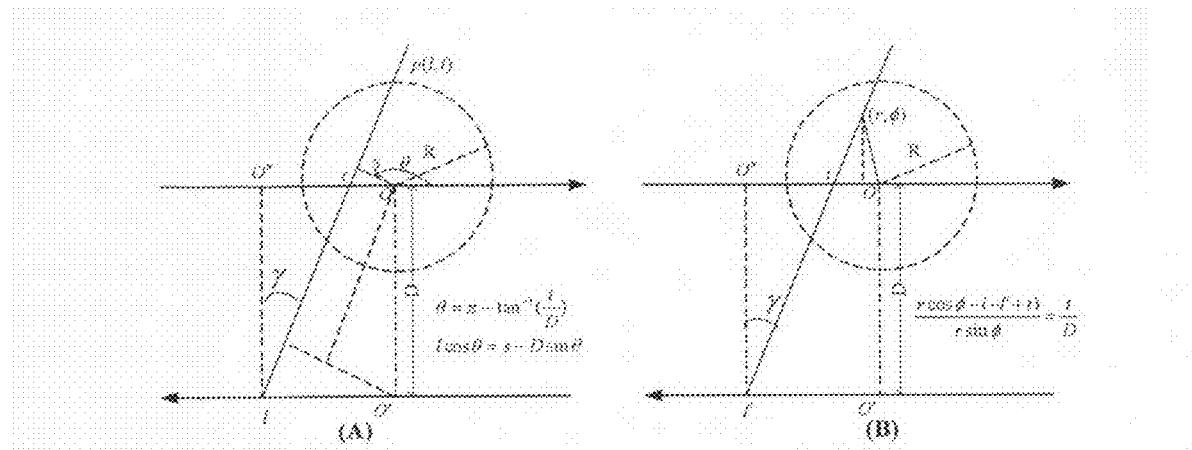
FIG. 5 is a schematic diagram for explaining the geometric relationship of the straight-line filtered back-projection procedure according to first embodiment of the present invention.

Below, the above Equation (1) will be derived by referring to FIGS. 1, 4 and 5. Before derivation, a procedure is firstly described for rebinning the linear scanned data into to parallel-beam scanned data.

According to the scan mode shown in FIG. 1, each detector corresponds to one projection angle, and while the object f(x,y) is moving, is equivalent to a parallel-beam scan under that angle. Referring to the projecting schematic diagram of FIG. 5, with respect to the detector matrix arranged with a constant spacing interval, the rebinning-to-parallel-beam formula for rebinning the linear scanned data into to parallel-beam scanned data is:

$$g(\theta, s) = p(l, t) \Big|_{s=\frac{D(-l+t)}{\sqrt{D^2+t^2}}}^{\theta=\pi-\tan^{-1}(\frac{t}{D})} \quad (6)$$

Here, $$g(\theta, s) = \int\int f(x, y)\delta(x\cos\theta + y\sin\theta - s)dxdy$$

represents projection data with a projection angle of θ and a distance from a rotation center of s in the parallel-beam scan. p(l,t) denotes projection data in the detector array when the object to be inspected relatively moves to a coordinate of l on the line.

With Equation (6), it can be achieved to rebin the straight-line trajectory scanned projection data into the projection data under the parallel-beam scan. However, in practical systems, since an infinite straight line is impossible, the rebinned data is not the parallel-beam scanned data of 180 degree of projection angles. That is to say, the data are incomplete for exact reconstruction.

With respect to linear scan, although the samplings to l and t may be uniform, both the samplings of projection angle θ and detector's position s under the corresponding parallel-beam scan are not uniform. Therefore, the rebinning procedure requires interpolations in the angular direction and the detector direction, which results in degrading the spatial resolution of the reconstruction.

Next, the reconstruction process of direct filtering and back-projecting the linear scanned data according to the present invention will be described.

The reconstruction formula of filtering and back-projecting under the parallel-beam scan is:

$$f(r, \phi) = \int_0^\pi \int_{-s_m}^{s_m} g(\theta, s)h(r\cos(\theta - \phi) - s)ds d\theta \quad (7)$$

Considering infinite straight-line trajectory and equi-distantly spaced detectors, using Equation (7), (θ,s) is replaced by (l,t) so that:

$$f(r, \phi) = \int_{-\infty}^\infty \int_{-\infty}^\infty \frac{1}{\sqrt{D^2+t^2}} p(-l+t, t)h(l'-l)dldt \quad (8)$$

Here, $l' = -r\cos\phi + \frac{tr\sin\phi}{D}$.

It is demonstrated as follows:

$$f(r, \phi) = \int_{-\infty}^{-\infty} \int_\infty^{-\infty} g\left(\pi - \tan^{-1}\left(\frac{t}{D}\right), \frac{D(-l+t)}{\sqrt{D^2+t^2}}\right) \times \quad (9)$$

$$h\left(r\cos\left(\pi - \tan^{-1}\left(\frac{t}{D}\right) - \phi\right) - \frac{D(-l+t)}{\sqrt{D^2+t^2}}\right)\frac{D^2}{(D^2+t^2)^{3/2}}dldt$$

Here, $\theta = \pi - \tan^{-1}\left(\frac{t}{D}\right)$, $s = \frac{D(-l+t)}{\sqrt{D^2+t^2}}$, $dsd\theta = \frac{D^2}{(D^2+t^2)^{3/2}}dldt$.

In the straight-line trajectory scan, $$g\left(\pi - \tan^{-1}\left(\frac{t}{D}\right), \frac{D(-l+t)}{\sqrt{D^2+t^2}}\right)$$

is replaced by p(l,t). Also, according to the geometric structure of FIG. 5, the following result can be obtained:

$$r\cos\left(\begin{array}{c}\pi - \\ \tan^{-1}\left(\frac{t}{D}\right) - \\ \phi\end{array}\right) - \frac{D(-l+t)}{\sqrt{D^2+t^2}} = -r\cos\phi\frac{D}{\sqrt{D^2+t^2}} + \quad (10)$$

$$r\sin\phi\frac{t}{\sqrt{D^2+t^2}} - $$

$$\frac{D(-l+t)}{\sqrt{D^2+t^2}}$$

-continued $$= \left(\frac{tr\sin\phi}{D} - \frac{l' - }{t}\right)\frac{D}{\sqrt{D^2+t^2}} +$$

$$r\sin\phi \frac{t}{\sqrt{D^2+t^2}} -$$

$$\frac{D(-l+t)}{\sqrt{D^2+t^2}}$$

$$= \frac{D}{\sqrt{D^2+t^2}}(l'+l-2t)$$

Here, $$l' = -r\cos\phi + \frac{tr\sin\phi}{D} + t,$$

which represents a space sampling position of the projection data passing through a point of (r,φ) and the $t^{th}$ detector element in the linear scan.

By substituting Equation (10) into Equation (9), using an equation $$h\left[\frac{D}{\sqrt{D^2+t^2}}(l'+l-2t)\right] = \frac{D^2+t^2}{D^2}h(l'+l-2t),$$

and substituting l=l−t, l'=l'−t, then the reconstructing formula (8) is achieved. For Equation (8), if q(l,t)=p(−l+t,t) is substituted into Equation (8), then $$f(r,\phi) = \int_{-\infty}^{\infty} \frac{1}{\sqrt{D^2+t^2}} Q(l',t) dt \qquad (11)$$

Here, $Q(l',t) = \int q(l,t)h(l'-l)dl.$

Actually, if the range of the straight-line trajectory is [−L, L] and the coverage of the detector is [−$t_m$,$t_m$], then the image reconstructed according to Equation (8) is not a ƒ(x,y) exactly but only an approximate one. Further more, if a three-dimension situation is considered, then the approximate estimation $\hat{f}(r,\phi,z)$ of the object ƒ(x,y,z) to be inspected can be expressed by Equation (1).

Above, the filtration, back-projection and reconstruction formula (1) of the straight-line trajectory scan and the inventive image reconstruction method in a case of equi-distantly spaced detector element arrangement are derived. Actually, the detector elements in the detector matrix can also be equi-angularly arranged. If the detector elements are arranged equi-angularly, similar to the above derivation, the filtration, back-projection and reconstruction formula can be changed to be:

$$\hat{f}(r,\phi,z) = \int_{-\gamma_m}^{\gamma_m} \frac{1}{\cos\gamma} Q\left(l',\gamma,z\frac{D}{D+r\sin\phi}\right)d\gamma \qquad (12)$$

-continued wherein, $$Q(l',\gamma,z) = \int q(l,\gamma,z)h(l'-l)dl \qquad (13)$$

$$q(l,\gamma,z) = p(-l + D\tan\gamma, \gamma, z) \qquad (14)$$

$$l' = -r\cos\phi + r\sin\phi\tan\gamma \qquad (15)$$

Here, the detector elements in the detector matrix are arranged equi-angularly, and the data p(l,γ,z) denotes a projection value at an angular position of γ in the $z^{th}$ slice of the detector matrix when the object 120 to be inspected moves to a coordinate of l on the line. It should be noted that γ and z are both equivalent values of the detector matrix onto the central line of the linear movement of the object. The notation ±$\gamma_m$ represent a minimum and a maximum angles of the detector matrix in the X-axis direction.

Therefore, in a case of equi-angularly spaced detector elements, the straight-line filtration, back-projection and reconstruction procedure is the as above, in which the reversing and shifting operation is performed according to Equation (14), the meaning of the convolution operation is the same as that in the equidistance case.

In other words, in the projection data conversion section 1651, the projection data p(l,γ,z) are reversed and shifted to obtain q(l,γ,z), wherein the projection data p(l,γ,z) denotes a projection value at an angular position of γ in the $z^{th}$ slice of the detector matrix when the object to be inspected relatively moves to a coordinate of l on the line.

In the filtration section 1652, the projection data q(l,γ,z) under quasi-parallel-beam scan are one-dimensionally convoluted with the convolutional kernel h in the l direction to obtain filtered projection data Q(l',γ,z).

In the back-projection section 1653, the filtered projection data Q(l',t,z) are back-projected with a weighting factor along the radiation projection direction to obtain the reconstructed image.

In order to precisely reconstruct images, the radiographic system shall be able to precisely measure or scale the following system parameters: a distance T from the radiation source to the detector matrix; a distance D from the radiation source to a central line of the linear movement; a linear movement speed v of the transporting unit; a sampling time interval Δt of the detector matrix; physical sizes of the detector including physical sizes of a single detector element and physical sizes of the detector matrix and the like.

The key feature of the imaging system according to the first embodiment of the present invention is it is straight-line trajectory scan not a circular or spiral trajectory scan. Since no rotation is needed and a nature procedure that objects to be inspected are linearly transported during the security inspection is used, the mechanical design is very simple.

In addition, due to the linear movement, the acceleration problem present in the circular or spiral scan is eliminated, and thus the custom clearance rate can be high. As compared with the traditional radioscopy, the present system can obtain tomographic images and/or stereoscopic images of the object, and solves the problem that the objects are overlapped in the perspective images.

In addition, the imaging system according to the first embodiment can obtain information acquired by a CT system and a stereoscopic imaging system.

In addition, the imaging system according to the first embodiment performance not has the large cone angle problem existing in the circular-orbit cone-beam CTs (the longer the vertical distance from the middle plane (central slice) is, the more the data loss is). This is because the arrangement of the projection data obtained by each slice of detectors is the same during the straight-line trajectory scan except that it is slant.

Figure 7:
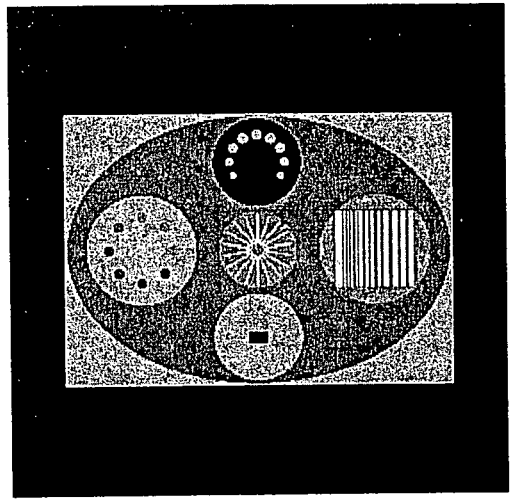
FIG. 7 is a performance comparison among numerical stimulated images (X-Y plane) obtained under different horizontal range of projection angles (also the coverage of the source and the detector) according to the first embodiment of the present invention.
Figure 7:
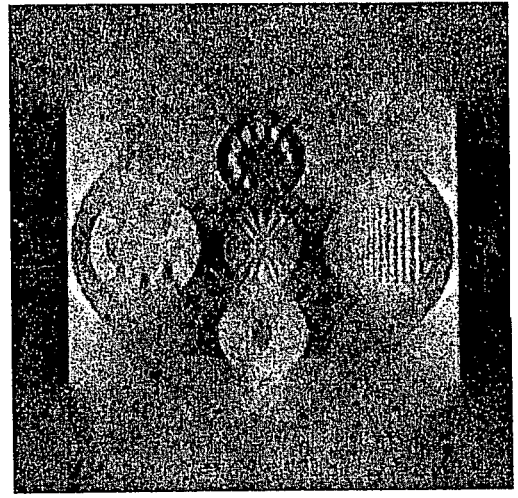
Figure 7:
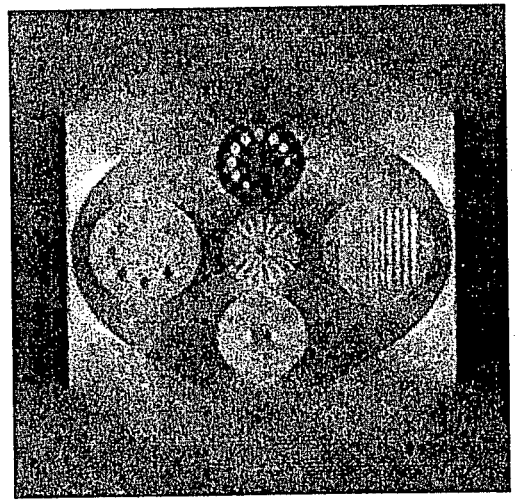
Figure 7:
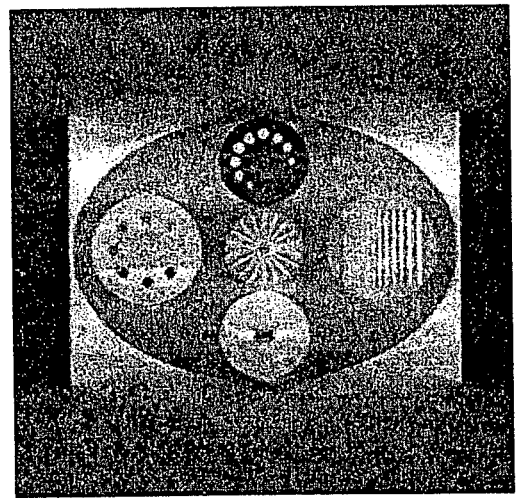

FIG. 7 is a performance comparison among numerical stimulated images (X-Y plane) obtained under different ranges of horizontal projection angles for the imaging system according to the first embodiment of the present invention, wherein (A) represents an original image of a model, (B) represents a stimulated image reconstructed by the imaging system according to the first embodiment of the present invention in a case of a range of 90 degree of horizontal projection angles, (C) represents a stimulated image reconstructed by the imaging system according to the first embodiment of the present invention in a case of a range of 120 degree of projection angles. (D) represents a stimulated image reconstructed by the imaging system according to the first embodiment of the present invention in a case of a range of 150 degree of projection angles. As shown, the quality of the reconstructed image is increased with the increasing of the range of projection angles.

Figure 8:
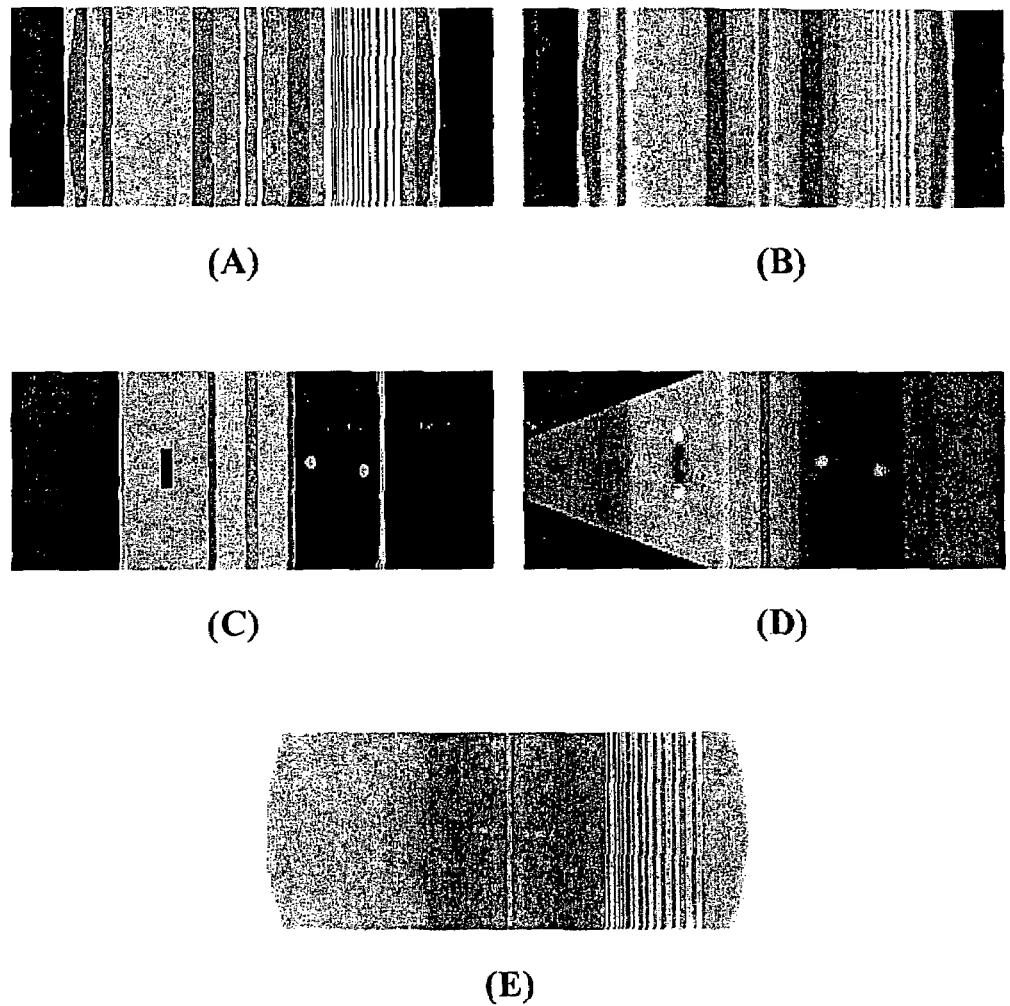
FIG. 8 is a performance comparison between the tomographic images (X-Z plane, Y-Z plane) and the perspective images reconstructed by the imaging system according to the first embodiment of the present invention.

FIG. 8 is a performance comparison between the tomographic images and the perspective images reconstructed by the imaging system according to the first embodiment of the present invention, wherein (A) represents an image of the central slice in the X-Z plane, (B) represents a stimulated image of the central slice in the X-Z plane reconstructed by the imaging system according to the first embodiment of the present invention, (C) represents an image of the central slice in the Y-Z plane, (D) represents a stimulated image of the central slice in the Y-Z plane reconstructed by the imaging system according to the first embodiment of the present invention, and (E) represents a stimulated perspective image obtained by the imaging system according to the first embodiment of the present invention.

Second Embodiment

Figure 6:
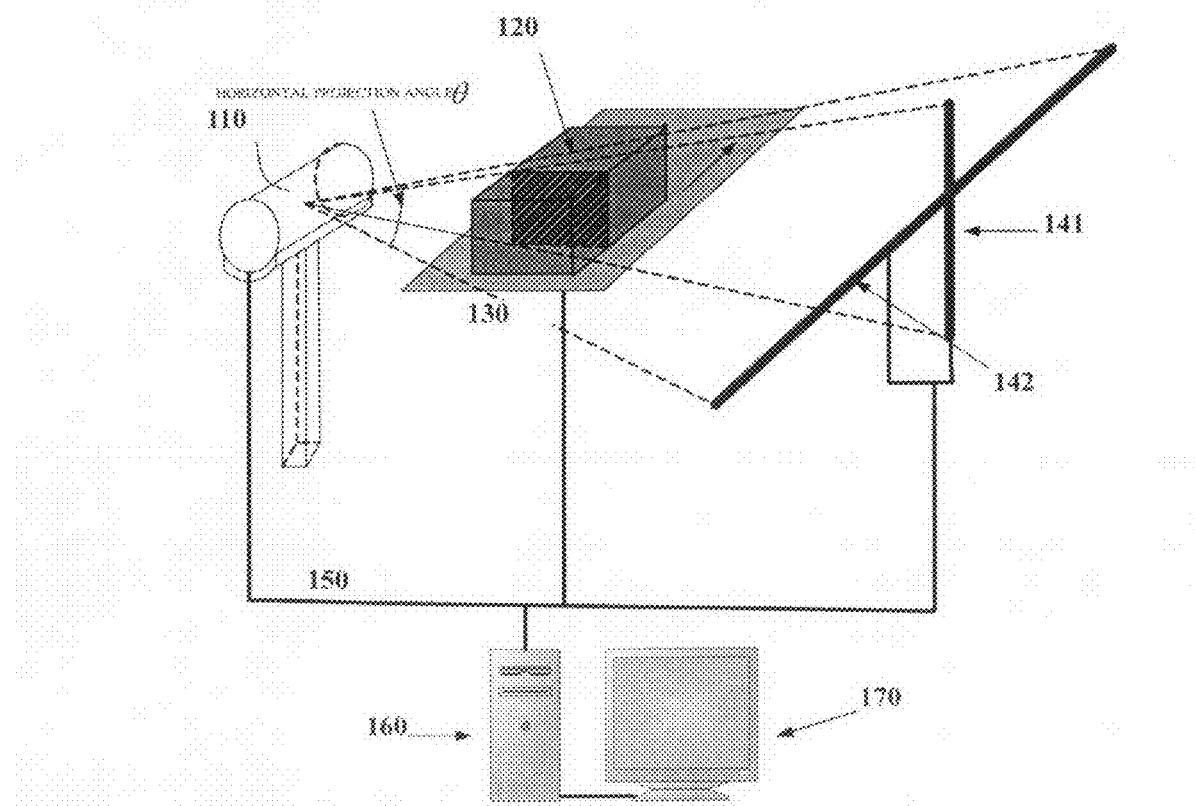
FIG. 6 is a structural diagram of the imaging system according to the second embodiment of the present invention.

FIG. 6 is a structural diagram of the imaging system according to the second embodiment of the present invention.

The imaging system according to the second embodiment of the present invention differs from the first embodiment in that another collinear detector array capable of moving up and down in the Z direction is further provided in a case where the detector array is of a single column (single slice, that is collinear array) so that a plurality of tomographic images can be obtained, and thus the stereoscopic imaging can be achieved with a small quantity of detector elements. Therefore, as compared with the first embodiment, the number of the detector elements in the detector array is dramatically decreased.

As shown in FIG. 6, the detector matrix in the data acquiring unit of the second embodiment includes two sets of single slice detector arrays 141 and 142 for acquiring the transmitted projection data of the cone-beam ray, one is horizontal, the other is vertical, and the detector elements included are generally arranged equidistantly or may be arranged equi-angularly. Similar to the first embodiment, the data acquiring unit further includes a readout circuit for reading out the projection data from the detectors, a logic control unit and the like.

In addition, the controller 163 included in the controlling and image processing unit 160 in the imaging system according to the second embodiment of the present invention can, besides those functions described in the first embodiment, control the horizontal single layer detector 142 to move up and down in the Z direction based on the instructions inputted by the user.

Thus, in addition to the advantages of the imaging system according to the first embodiment, the imaging system according to the second embodiment can further decrease the quantity of the detector elements, simplify the structure of the imaging system, and reduce the cost of the imaging system.

Figure 9:
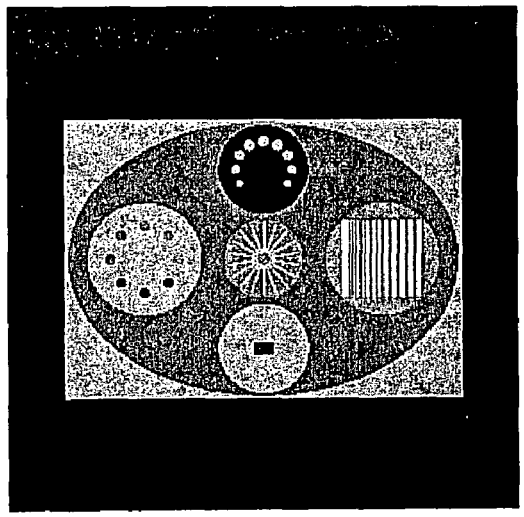
FIG. 9 is a performance comparison among numerical stimulated images (X-Y plane) obtained under different horizontal range of projection angles (also the coverage of the source and the detector) according to the second embodiment of the present invention.
Figure 9:
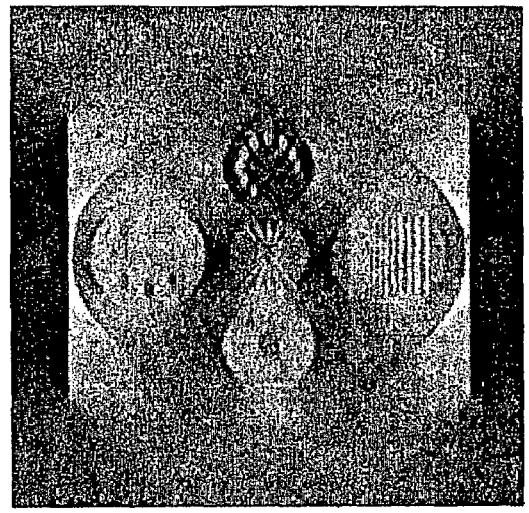
Figure 9:
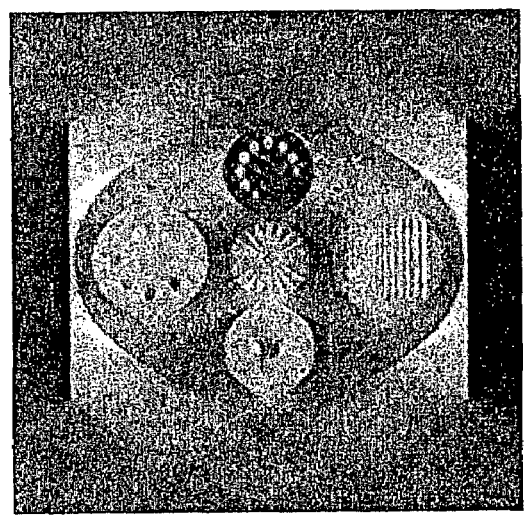
Figure 9:
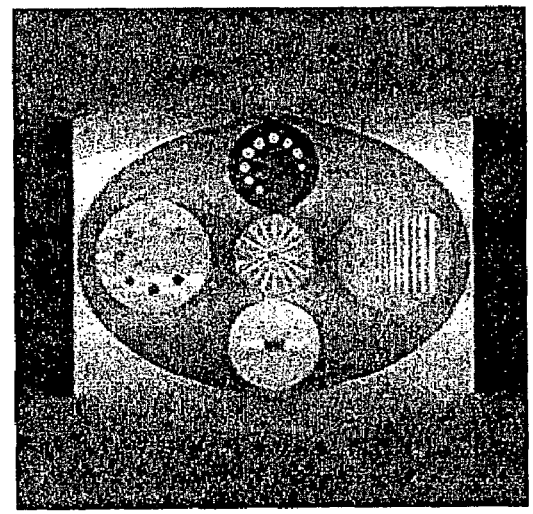

FIG. 9 is a performance comparison among numerical stimulated images (X-Y plane) obtained under different ranges of projection angles for the imaging system according to the second embodiment of the present invention, wherein (A) represents an original image of the model, (B) represents a stimulated image reconstructed by the imaging system according to the second embodiment of the present invention in a case of a range of 90 degree of horizontal projection angles, (C) represents a stimulated image reconstructed by the imaging system according to the second embodiment of the present invention in a case of a range of 120 degree of horizontal projection angles, and (D) represents a stimulated image reconstructed by the imaging system according to the second embodiment of the present invention in a case of a range of 150 degree of horizontal projection angles. As shown, the imaging system according to the second embodiment has almost the same imaging quality with the first embodiment.

Figure 10:
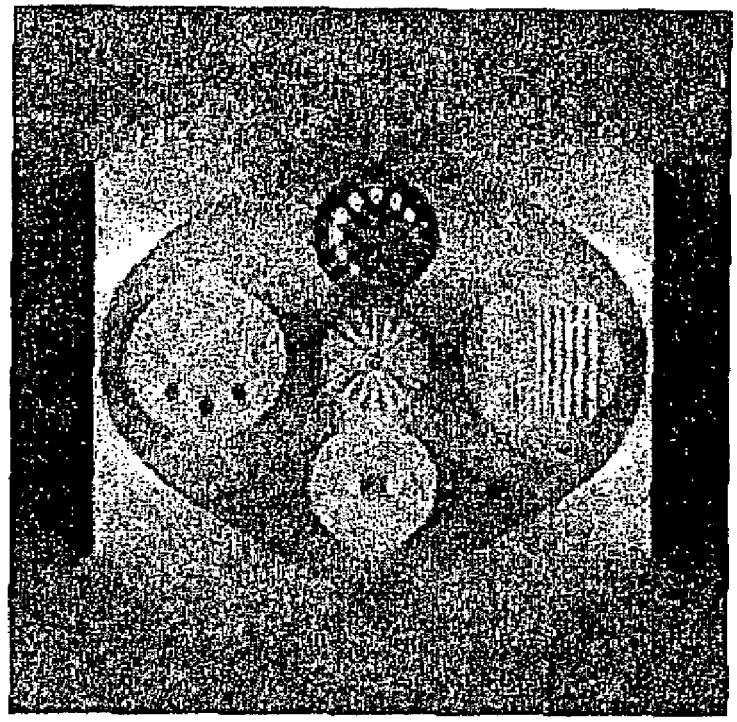
FIG. 10 shows the tomographic images (X-Y plane) and the perspective images reconstructed by the imaging system according to the second embodiment of the present invention.
Figure 10:
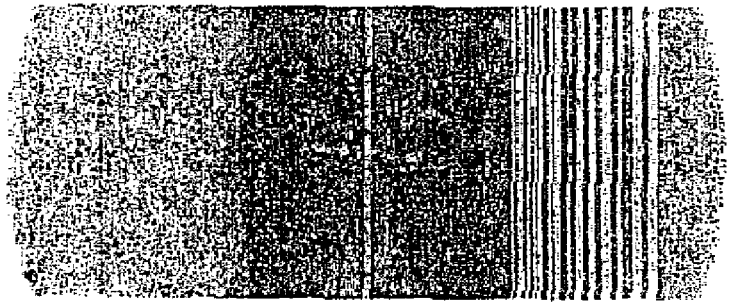

FIG. 10 shows the tomographic images (X-Y plane) and the perspective images reconstructed by the imaging system according to the second embodiment of the present invention, wherein (A) represents an image of the central slice in the X-Y plane, and (B) represents a stimulated image of the central slice in the X-Y plane reconstructed by the imaging system according to the second embodiment of the present invention. As shown, the imaging system according to the second embodiment has almost the same imaging quality with the first embodiment.

Hereto, the present invention has already been described with the preferred embodiments thereof. It should be understood by those skilled in the art, many variations, substitutions and additions are possible without departing from the spirits and scopes of the present invention. Therefore, the scopes of the invention should not be construed to be limited to the above specific embodiments but should be limited by the appended claims.

What is claimed is:

1. An imaging system comprising:

radiation generating means including at least one radiation source for generating radiations;

data acquiring means including a detector matrix opposite to the radiation source for obtaining projection data by receiving radiations penetrated through an object to be inspected;

transporting means for making the object to be inspected between the radiation source and the detector matrix linearly moving relative to the radiation source and the detector matrix; and controlling and image processing means for controlling the radiation generating means, the data acquiring means and the transporting means, and for reconstructing an image of the object to be inspected from the projection data;

wherein the controlling and image processing means includes:

a projection data conversion section for converting the projection data into projection data under quasi-parallel-beam scan;

a filtration section for obtaining filtered projection data by convoluting the projection data under quasi-parallel-beam scan with a predetermined convolutional kernel; and a back-projection section for reconstructing the image by back-projecting the filtered projection data with a weighting factor;

wherein the imaging system uses straight-line trajectory scan and straight-line filtered back projection, in which the filter section one-dimensionally convolutes the projection data in the direction of the line along which the object to be inspected is moving, and the back-projection section back-projects the filtered projection data in the direction of radiation projection.

2. The imaging system according to claim 1, wherein the plurality of detector elements are equi-distantly arranged.

3. The imaging system according to claim 2, wherein the projection data conversion section reverses and shifts the projection data $p(l,t,z)$ to obtain the projection data $q(l,t,z)$ under quasi-parallel-beam scan, wherein the projection data $p(l,t,z)$ denotes a projection value at a coordinate of t in the $z^{th}$ slice of the detector when the object to be inspected relatively moves to a coordinate of l on the line;

the filtration section one-dimension convolutes the projection data $q(l,t,z)$ under quasi-parallel-beam scan with the predetermined convolutional kernel in the l direction to obtain the filtered projection data $Q(l',t,z)$; and the back-projection section back-projects the filtered projection data $Q(l',t,z)$ along the radiation projection direction a weighting factor to obtain the reconstructed image.

4. The imaging system according to claim 1, wherein the plurality of detector elements are equi-angularly arranged.

5. The imaging system according to claim 4, wherein the projection data conversion section reverses and shifts the projection data $p(l,\gamma,z)$ to obtain the projection data $q(l,\gamma,z)$ under quasi-parallel-beam scan, wherein the projection data $p(l,\gamma,z)$ denotes a projection value at an angular position of $\gamma$ in the $z^{th}$ slice of the detector matrix when the object to be inspected relatively moves to a coordinate of l on the line;

the filtration section one-dimension convolutes the projection data $q(l,\gamma,z)$ under quasi-parallel-beam scan with the predetermined convolutional kernel in the l direction to obtain the filtered projection data $Q(l',\gamma,z)$; and the back-projection section back-projects the filtered projection data $Q(l',\gamma,z)$ with along the radiation projection direction a weighting factor to obtain the reconstructed image.

6. The imaging system according to claim 1, wherein the plurality of detector elements are solid detector elements, gas detector elements or semiconductor detector elements.

7. The imaging system according to claim 1, wherein the radiation source is an X-ray accelerator, an X-ray tube or a radioisotope.

8. The imaging system according to claim 1, wherein a horizontal range of projection angles is more than 90 degree.

9. The imaging system according to claim 8, wherein the detector matrix comprises a plannar detector containing a plurality of detector elements.

10. The imaging system according to claim 8, wherein the detector matrix comprises a collinear detector provided vertically and containing a plurality of detector elements.

11. The imaging system according to claim 10, wherein the detector matrix further comprises another collinear detector provided horizontally and containing a plurality of detector elements.

12. The imaging system according to claim 11, wherein the another collinear detector horizontally provided has a variable position in the vertical direction.

* * * * *